(12) United States Patent
Bergman et al.

(10) Patent No.: US 9,518,851 B2
(45) Date of Patent: Dec. 13, 2016

(54) PROBES FOR INSPECTION SYSTEM FOR SUBSTANTIALLY ROUND HOLE

(71) Applicant: General Electric Company, Schenectady, NY (US)

(72) Inventors: Robert William Bergman, Scotia, NY (US); Thomas James Batzinger, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 141 days.

(21) Appl. No.: 14/559,278

(22) Filed: Dec. 3, 2014

(65) Prior Publication Data

US 2016/0161300 A1 Jun. 9, 2016

(51) Int. Cl.
| | | |
|---|---|---|
| G01D 11/30 | (2006.01) | |
| G01N 27/90 | (2006.01) | |
| G01M 15/14 | (2006.01) | |
| G01N 29/04 | (2006.01) | |
| G01N 29/22 | (2006.01) | |

(52) U.S. Cl.
CPC .............. *G01D 11/30* (2013.01); *G01M 15/14* (2013.01); *G01N 27/9006* (2013.01); *G01N 29/043* (2013.01); *G01N 29/225* (2013.01); *G01N 2291/2636* (2013.01)

(58) Field of Classification Search
None
See application file for complete search history.

(56) References Cited

U.S. PATENT DOCUMENTS

| | | | |
|---|---|---|---|
| 3,001,130 A | | 9/1961 | McClurg et al. |
| 3,238,448 A | | 3/1966 | Wood et al. |
| 4,468,623 A | * | 8/1984 | Gianzero .................. G01V 3/20 324/355 |
| 4,976,150 A | * | 12/1990 | Deka .................. G01N 29/2437 73/644 |
| 6,191,588 B1 | * | 2/2001 | Chen ........................ G01V 3/20 324/367 |
| 6,339,326 B1 | | 1/2002 | Trantow |
| 6,339,331 B1 | | 1/2002 | Ruzzo |
| 6,452,384 B1 | | 9/2002 | Becker et al. |
| 6,741,074 B2 | | 5/2004 | DeBlock et al. |
| 7,190,162 B2 | | 3/2007 | Tenley et al. |
| 7,436,992 B2 | | 10/2008 | Suh et al. |
| 7,458,289 B2 | | 12/2008 | Houldey et al. |
| 7,579,830 B2 | | 8/2009 | Roney et al. |
| 7,768,259 B2 | | 8/2010 | Cabanis et al. |
| 7,800,364 B2 | | 9/2010 | Briffa et al. |
| 7,952,348 B2 | | 5/2011 | Sun et al. |
| 8,008,913 B2 | | 8/2011 | Qiao et al. |
| 8,179,132 B2 | | 5/2012 | Wu et al. |
| 8,240,042 B2 | | 8/2012 | Williams et al. |
| 8,269,489 B2 | | 9/2012 | Wang et al. |
| 8,578,780 B2 | * | 11/2013 | Meier .................. G01N 29/043 73/632 |
| 8,680,852 B2 | | 3/2014 | Daly et al. |

* cited by examiner

*Primary Examiner* — Paresh Patel
(74) *Attorney, Agent, or Firm* — Ernest G. Cusick; Hoffman Warnick, LLC

(57) ABSTRACT

Probes for an inspection system for a substantially round hole in a material are provided. One version of the probe may include a flexible sheet shaped and biased to substantially conform with a portion of an interior of the substantially round hole; and a plurality of sensors disposed on the flexible sheet, each sensor configured to transmit a nondestructive signal into the material for inspecting the substantially round hole.

19 Claims, 5 Drawing Sheets

PROBES FOR INSPECTION SYSTEM FOR SUBSTANTIALLY ROUND HOLE

BACKGROUND OF THE INVENTION

The disclosure relates generally to inspection systems, and more particularly, to probes for an inspection system for a substantially round hole using eddy currents or ultrasound.

Industrial machines such as gas turbines have numerous parts having holes therein that require inspection using eddy currents or ultrasound. For example, a bolt hole in a gas turbine part may require such inspection to identify cracks, etc. One challenge in using eddy current and ultrasonic inspection methods is that they require very precise manipulation of the inspection probe. Performing inspections on inner diameter surfaces of larger diameters (e.g., over 2.5 centimeters) makes probe manipulation very difficult. Another challenge is that a probe that employs a single sensor necessitates very long inspection times due to proper inspection coverage requirements. In addition, a single sensor probe requires complex manipulation to ensure adequate inspection coverage.

BRIEF DESCRIPTION OF THE INVENTION

A first aspect of the disclosure provides a probe for an inspection system for a substantially round hole in a material, the probe comprising: a flexible sheet shaped and biased to substantially conform with a portion of an interior of the substantially round hole; and a plurality of sensors disposed on the flexible sheet, each sensor configured to transmit a non-destructive signal into the material for inspecting the substantially round hole.

A second aspect of the disclosure provides a probe for an inspection system for a substantially round hole in a material, the probe comprising: an elongated sensor support; a bearing plate configured to rotatably support the elongated sensor support in a position in the substantially round hole; a sensor mount surface shaped to substantially conform with a portion of an interior of the substantially round hole; a plurality of sensors disposed on the sensor mount surface, each sensor configured to transmit a non-destructive signal into the material for inspecting the substantially round hole; and a biasing element coupling the sensor mount surface and the elongated sensor support, the biasing element biasing the sensor mount surface to substantially conform with the portion of the interior of the substantially round hole.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure provides probes for an inspection system for a substantially round hole.

Figure 1:
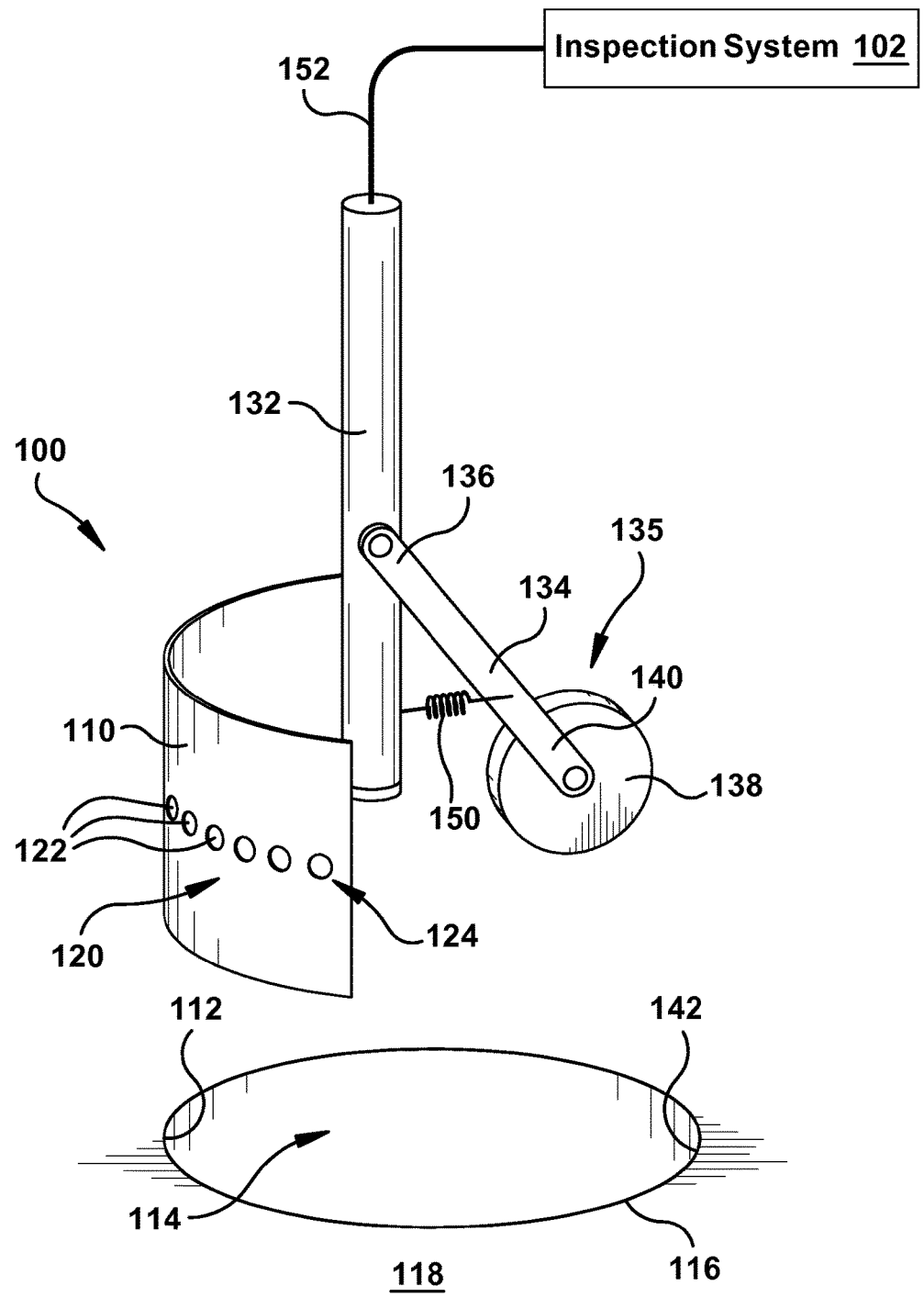
FIG. 1 shows a perspective view of a probe for an inspection system for a substantially round hole according to one embodiment of the invention.
Figure 2:
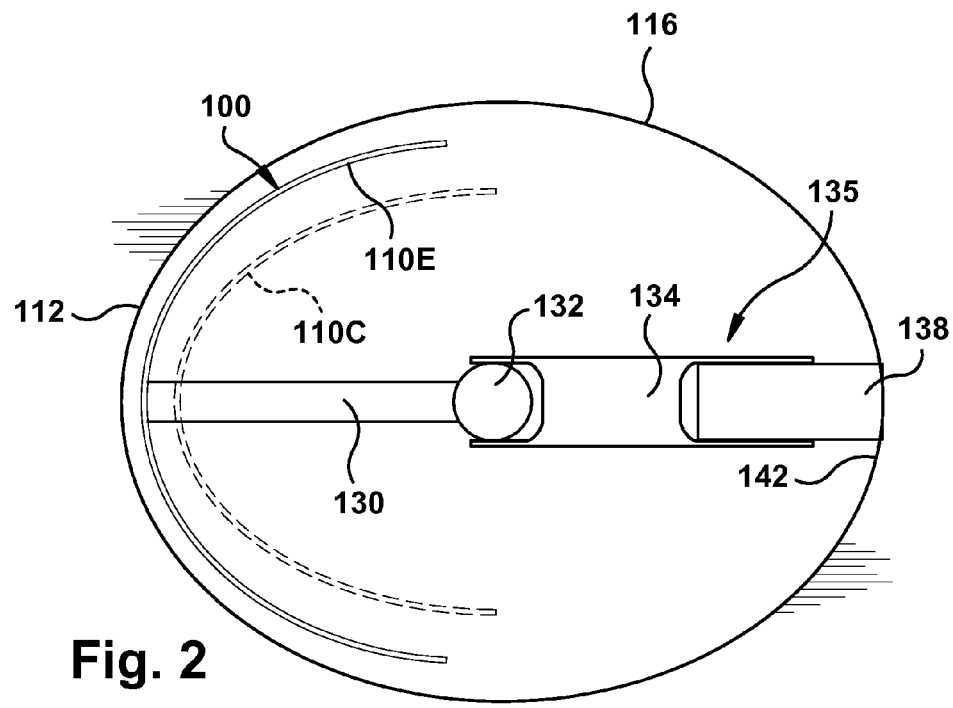
FIG. 2 shows an enlarged plan view of a guide member on the probe of FIG. 1.
Figure 3:
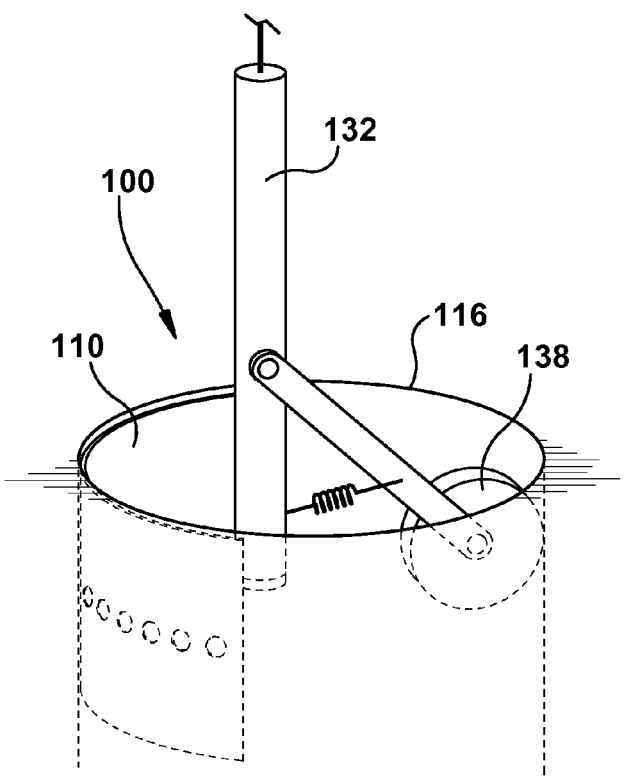
FIG. 3 shows a perspective view of the probe of FIG. 1 in operation.

Referring to FIGS. 1-3, in one embodiment, a probe 100 for an inspection system 102 for a substantially round hole in a material is illustrated. Inspection system 102 may include any now known or later developed eddy current or ultrasound inspection system capable of operatively coupling with a probe according to the invention. As understood, inspection system 102 includes a control system for transmitting either an eddy current or ultrasound signal through a probe, such as probe 100 in FIGS. 1-3 or probe 200 in FIGS. 4-6, receive a return signal and analyze the return signal such that the structure of the material upon which the signals are transmitted can be analyzed and/or imaged. Such inspection systems 102 are capable of, among other things, identifying flaws in the material such as cracks or other imperfections.

As used herein, a "substantially round hole" refers to a hole in a material, e.g., steel, aluminum or other metal or alloy thereof, that has at least a portion that has a rounded, oval, circular or near circular cross-section. In one example, the hole may be a threaded opening such as a bolt hole in a part of a gas turbine. A large variety of alternative examples will be apparent to one with skill in the art.

Referring to FIG. 1, probe 100 may include a flexible sheet 110 shaped and biased to substantially conform with a portion 112 of an interior 114 of a substantially round hole 116 in a material 118. In one embodiment, flexible sheet 110 may include a polystyrene substrate; however, a variety of other flexible sheet materials may be employed such as but not limited to polytetrafluorethylene (PTFE) and vinyls. A plurality of sensors 120 may be disposed on flexible sheet 110 such that each sensor 122 can transmit a non-destructive signal into material 118 for inspecting the substantially round hole, i.e., by inspection system 102 analyzing a return signal received by sensors 122. As noted herein, the non-destructive signal may include one of an eddy current signal and an ultrasound signal. Each sensor 122 may take any appropriate form based on the type of signal used, e.g., any combination of coils for eddy current, or an ultrasound transducer for transmission and reception of ultrasonic signals. In one embodiment, as shown in FIG. 1, plurality of sensors 120 may extend along a line 124 on flexible sheet 110, and along substantially the entire length of flexible sheet 110. In this manner, as probe 100 enters or exits hole 116, it is evaluating at least half of the hole, e.g., at least 180° of the round hole. While a linear arrangement has been illustrated, other arrangements may be provided depending on the shape of portion 112. For example, two lines of sensors, a sinusoidal line, an array of sensors, etc., may be employed.

Flexible sheet 110 may be initially shaped to substantially conform to portion 112, e.g., by having a particular length and radius of curvature. For example, the polystyrene substrate may have a shape configured to substantially conform to portion 112 of interior 114 of substantially round hole 116. For example, if hole 116 has a diameter of 1.2 centimeters, flexible sheet 110 may have a radius of curvature of 0.6 cm (radius of hole 116) and a length approximately 1.9 cm (just over half of the circumference of hole 116). In addition, as shown in FIG. 2, flexible sheet may be flexible between a first, compressed position (110C dashed line in FIG. 2) sized to fit into an end of substantially round hole 116 and a second, expanded position (110E solid line in FIG. 2) sized to substantially conform with portion 112 of interior 114 of substantially round hole 116. In this fashion, probe 100 can be readily inserted into hole 116 without a drastic amount of manipulation in the first, compressed position, and then allowed to expand for use to the second, expanded position. In one example, as shown in FIG. 1, portion 112 may include a substantially semi-circular portion of interior 114 of substantially round hole 116, and flexible sheet 110 may be sized to substantially conform with the substantially semi-circular portion of the interior of the substantially round hole. Alternatively, as shown in FIG. 2, portion 112 can be more arcuate than substantially semi-circular where hole 116 is not exactly circular.

As shown in FIGS. 1 and 2, probe 100 may also include a probe support 130 (FIG. 2 only) coupled to flexible sheet 110 for supporting the flexible sheet relative to substantially round hole 116. A handle 132 may be coupled to probe support 130 for controlling a position of the probe. Probe support 130 and handle 132 may be made of any material having sufficient strength to manipulate the position of flexible sheet 110, e.g., a metal or hard plastic. Probe support 130 may be coupled to flexible sheet in any now known or later developed fashion, e.g., mechanical fasteners such as a screw, adhesives, etc. Probe support 130 and handle 132 may be coupled in a similar fashion or may be made as a one-piece structure.

Although not necessary in all cases, in one embodiment, a guide 135 that is movable with flexible sheet 110 and relative to an opposing portion 142 (to portion 112) of interior 114 of hole 116 to guide the flexible sheet along the portion, may be provided. In one embodiment, guide 135 may include a guide support 134 pivotally coupled to handle 132, e.g., by a pin, at a first end 136 of the guide support. Guide support 134 may be positioned within a groove (not shown) within handle 132 or simply be pivotally coupled to an exterior of the handle. A guide member 138 may be coupled to a second end 140 of guide support 134 for engaging opposing portion 142 of interior 114 of substantially round hole 116 from flexible sheet 110. In the example shown, guide member 138 includes a wheel rotatably coupled to second end 140; however, any variety of structures capable of pressing against opposing portion 142 and moving therealong, e.g., by rolling or sliding, may be employed. For example, a slide member or skid of a block of material may be equally applicable. Guide member 138 may be made of any material capable of withstanding engagement, rolling, sliding or otherwise, with opposing portion 142, e.g., a metal or plastic. Guide support 134 may be made of the same material as probe support 130 or handle 132. As shown in FIG. 1, guide 135 may also include a biasing element 150 to bias guide support 134 to press guide member 138 against opposing portion 142. In this fashion, guide member 138 is movable with flexible sheet 110 (and sensors 120) and relative to opposing portion 142 to guide the flexible sheet 110 in a substantially conforming manner along portion 112. Biasing element 150 may take a variety of forms, e.g., a spring, a pneumatic ram, a hydraulic ram, etc. Guide support 134 and/or biasing element 150 may be changed, e.g., in size, strength, location, etc., to accommodate different sized holes 116. Where applicable, control of biasing element 150 can be made via inspection system 102, e.g., using pneumatic, electrical or hydraulic controls.

As illustrated in FIG. 1, any wiring 152 that may be necessary to couple inspection system 102 to sensors 120 or biasing element 150 can be placed along or within handle 132 and/or along or within probe support 130. Any now known or later developed transition seals or hardware necessary to protect the wiring relative to openings, e.g., within the handle, or moving parts may be employed.

In operation, as shown in FIGS. 2 and 3, probe 100 will allow for an inspection of a hole 116 by feeding the probe containing sensors 120 into the hole. As probe 100 is directed into hole 116, sensors transmit/receive an appropriate signal into about half of the hole, e.g., approximately 180°, resulting in an inspection of about half the hole. Once probe 100 is fed through in one direction, probe 100 may be rotated approximately 180° and pulled back through the hole resulting in an inspection of the remaining half of the hole. During insertion and retraction, flexible sheet 110, perhaps with guide member 138 where employed, maintains good conformance with portion 112 of interior 114 of hole 116, providing good quality eddy current or ultrasound data for inspection system 102.

Figure 4:
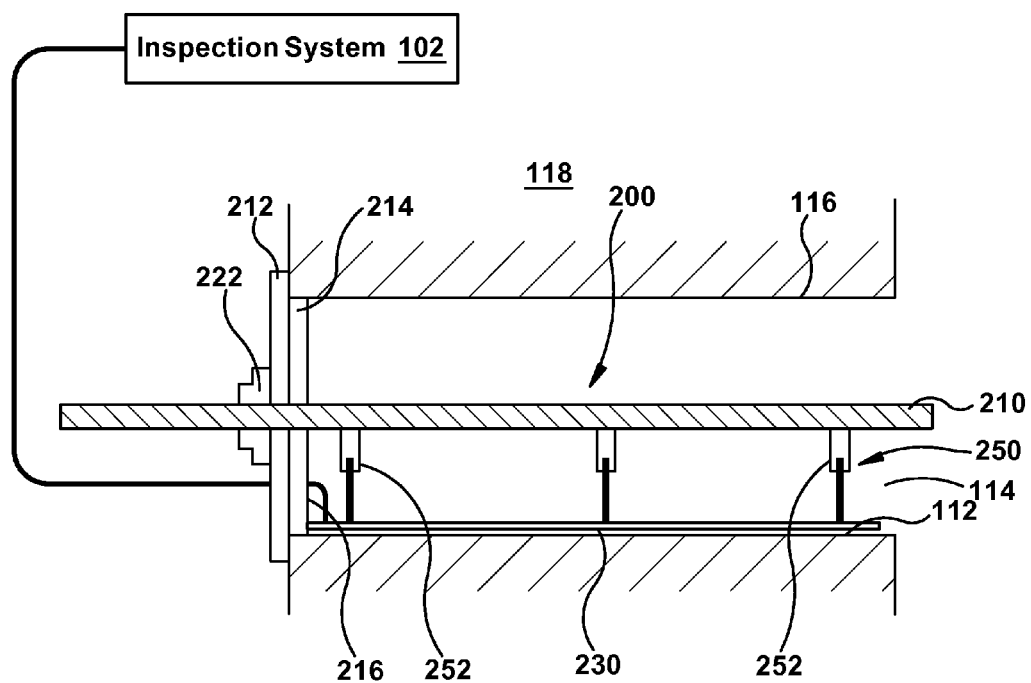
FIG. 4 shows a perspective view of a probe for an inspection system for a substantially round hole according to another embodiment of the invention.
Figure 5:
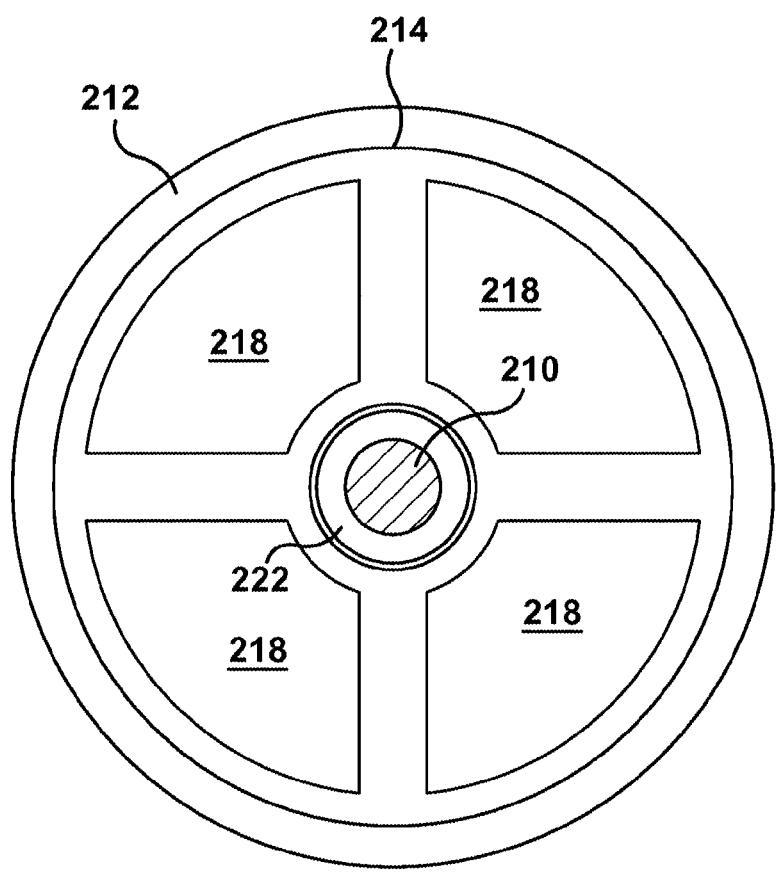
FIG. 5 shows a side view of a bearing plate of the probe of FIG. 1 according to an embodiment of the invention.
Figure 6:
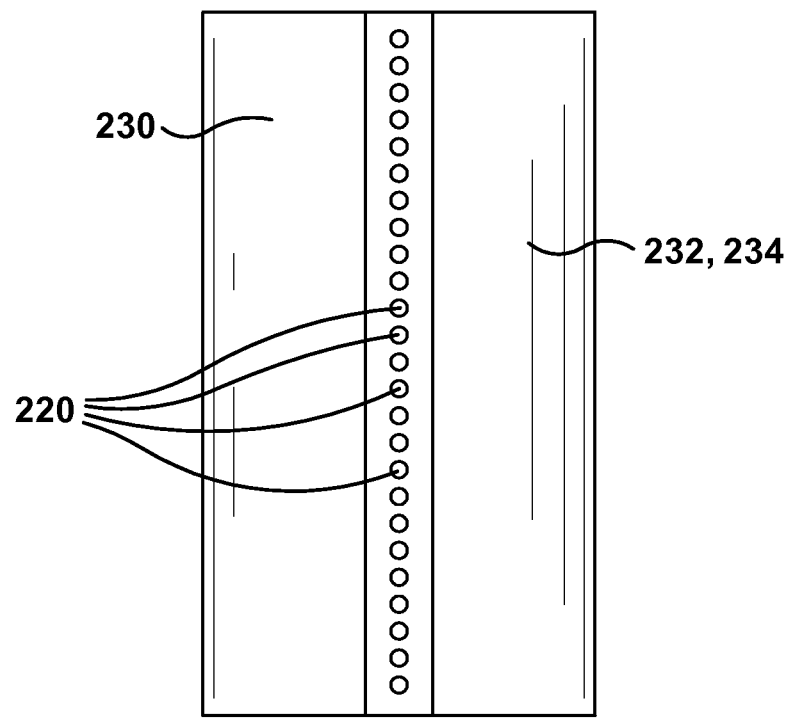
FIG. 6 shows a plan view of a sensor mount surface of the probe of FIG. 4 according to an embodiment of the invention.

Turning to FIGS. 4-6, another embodiment of a probe 200 for inspection system 102 for substantially round hole 116 in material 118 is illustrated. In this embodiment, probe 200 may include an elongated sensor support 210. Elongated sensor support 210 is elongated sufficiently to ensure full sensor coverage over a length of hole 116, i.e., all relevant parts of hole 116 are capable of being evaluated. A bearing plate 212 is configured to rotatably support elongated sensor support 210 in a position in substantially round hole 116. As illustrated, bearing plate 212 positions elongated sensor support 210 such that is centered in hole 116; however, this is not necessary in all instances, e.g., for oblong rounded holes. In any event, bearing plate 212 may include a mount surface 214 configured to mate with an end 116 of substantially round hole 116 to position elongated sensor support 210. Mount surface 214 may be shaped to match end 116 such that bearing plate 212 positions sensor support 210 appropriately, and may turn in end 116 where end 116 and support 214 are substantially concentric. As shown in FIG. 5, bearing plate 212 may also include at least one passage 218 therethrough to allow wiring to be coupled to sensors 220 (FIGS. 6 and 7) (where necessary), viewing into hole 116, etc. While four passages are illustrated, any number may be used. While mount surface 214 is illustrated as a substantially circular member in FIG. 5, mount surface 214 need not be continuous as circumferentially space members on bearing plate 212 may be employed.

Elongated sensor support 210 is rotatably coupled to bearing plate 212 by a bearing 222 that may limit rotation of elongated bearing support 210 to just greater than 360° (e.g., 362°, 365°, 370°, etc.), the purpose of which will be described herein. "Just greater than 360°" can be any amount close to 360° that ensures all of hole has been evaluated without a large amount of overlap. Bearing 222 may limit rotation of elongated bearing support 210 in any known fashion, e.g., rotational stops on, in or adjacent bearing 222 and/or on, in or adjacent support 210. In addition, a starting location can be set or keyed with bearing 222 to ensure that all measurements start at the same location. Support 210, bearing plate 212 and bearing 222 may be made of any material having sufficient strength to support sensors 220, e.g., a metal or hard plastic.

Figure 7:
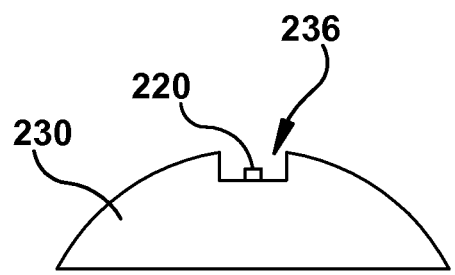
FIG. 7 shows a side view of a sensor mount surface of the probe of FIG. 4 according to an embodiment of the invention.

FIG. 6 shows a plan view and FIG. 7 shows a side view of a sensor mount surface 230 of probe 200 of FIG. 4 according to an embodiment of the invention. As illustrated, sensor mount surface 230 may be shaped to substantially conform with portion 112 (FIG. 4) of interior 114 (FIG. 4) of substantially round hole 116 (FIG. 4). As noted herein, portion 112 may include a substantially semi-circular portion of interior 114 of substantially round hole 116, and the sensor mount surface is sized to substantially conform with at least some portion of the substantially semi-circular portion of the interior of the substantially round hole. Accordingly, in one embodiment, sensor mount surface 230 may have a fixed curvature to accommodate the smallest hole 116, i.e., portion 112, for which probe 200 (FIG. 4) may be applied. In this case, sensor mount surface 230 may be made of a rigid material 232 such as a metal or hard plastic. In another embodiment, sensor mount surface 214 may include a flexible sheet 234 shaped and biased to substantially conform with portion 112 of interior 114 of substantially round hole 116. Flexible sheet 234 may be of the same material as flexible sheet 110, described herein, e.g., a polystyrene substrate. As with flexible sheet 110, flexible sheet 234 may be flexible between a compressed and expanded state. Flexible sheet 234 along with elongated sensor support 210 each have a length ensure complete measurements of the length of hole 116, and may be changed in length to accommodate different length holes.

As shown in the plan view portion of FIG. 6, a plurality of sensors 220 may be disposed on sensor mount surface 230. Each sensor 220 may be configured to transmit a non-destructive signal into the material for inspecting substantially round hole 116 (FIG. 4). As noted herein, the non-destructive signal may include an eddy current signal or an ultrasound signal. In addition, plurality of sensors 220 may be arranged on sensor mount surface 230 in a wide variety of arrangements to accommodate different holes 116, e.g., parallel lines, sinusoidal, arrays, etc. In the embodiment illustrated, for example, sensors 220 extend along a longitudinal line on sensor mount surface 230, and may extend along substantially an entire length of sensor mount surface 230. In one embodiment, sensor mount surface 230 may include, as shown in the side view of FIG. 7, a channel 236 along a longitudinal axis thereof. Plurality of sensors 220 may be disposed within channel 236 to protect sensors 220 in situations where protection is necessary such as in hole 116 having a rough surface interior.

Returning to FIG. 4, probe 200 may also include a biasing element 250 coupling sensor mount surface 230 and elongated sensor support 210. Biasing element 250 biases sensor mount surface 230 to substantially conform with portion 112 of interior 114 of substantially round hole 116. In the example shown, biasing element 250 includes a plurality of pneumatic rams 252 distributed along a length of sensor mount surface 230. Although three rams 252 are shown, any number may be employed to sufficiently bias sensor mount surface 230. In addition, while pneumatic rams are illustrated, biasing element may employ any form of biasing system now known or later developed such as but not limited to springs, hydraulic rams, etc. The size and/or location of biasing element 150 may be changed to accommodate different sized holes 116. Biasing element 250, e.g., rams 252, may be coupled to sensor support 210 and sensor mount surface 230 using any now known or later developed solution, e.g., mechanical fasteners such as hinges, pivot joints, screws, etc.; welding; adhesives; etc. In addition, while biasing element 250 is illustrated as having rams 252 arranged in a linear fashion relative to sensor mount surface 230, the rams or other biasing elements may be circumferentially displaced along the arc sensor mount surface 230 in order to distribute the bias across the circumference of the surface. Furthermore, although only one ram is shown at each axial location, one or more rams or other biasing elements may be employed at each axial location along support 210.

In operation, as shown in FIG. 4, probe 200 will allow for an inspection of hole 116. Once probe 200 is placed in hole 116, biasing element 250 can be activated, e.g., by applying pneumatic pressure to rams 252, to ensure sensor mount surface 234 adequately contacts or is close enough to portion 112 for sensors 220 to operate. At this point, inspection system 100 can activate sensors 220 and sensor support 210 can be rotated to expose an entirety of hole 116 to sensors 220 through just greater than 360° rotation (e.g., 361°, 364°, 369°, etc.) of sensor support 210. In this fashion, a complete inspection of hole 116 can be completed with biasing element 250 maintaining good conformance with portion 112 of interior 114 of hole 116, providing good quality eddy current or ultrasound data for inspection system 102.

Either of the embodiments provides information may be used to extend the operation life of industrial parts having holes 116 therein, e.g., gas turbine components.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:
1. A probe for an inspection system for a substantially round hole in a material, the probe comprising:
 a flexible sheet shaped and biased to substantially conform with a portion of an interior of the substantially round hole;

a plurality of sensors disposed on the flexible sheet, each sensor configured to transmit a non-destructive signal into the material for inspecting the substantially round hole;

a probe support coupled to the flexible sheet for supporting the flexible sheet relative to the substantially round hole;

a handle coupled to the probe support for controlling a position of the probe;

a guide support pivotally coupled to the handle at a first end of the guide support;

a guide member coupled to a second end of the guide support for engaging an opposing portion of the interior of the substantially round hole from the flexible sheet; and a biasing element to bias the guide support to press the guide member against the opposing portion, the guide member movable with the flexible sheet and relative to the opposing portion to guide the flexible sheet along the portion.

2. The probe of claim 1, wherein the non-destructive signal includes one of an eddy current signal and an ultrasound signal.

3. The probe of claim 1, wherein the flexible sheet includes a polystyrene substrate.

4. The probe of claim 3, wherein the polystyrene substrate has a shape configured to substantially conform to the portion of the interior of the substantially round hole.

5. The probe of claim 1, wherein the guide member includes a wheel.

6. The probe of claim 1, wherein the flexible sheet is flexible between a first, compressed position sized to fit into an end of the substantially round hole and a second, expanded position sized to substantially conform with the portion of an interior of the substantially round hole.

7. The probe of claim 1, wherein the portion includes a substantially semi-circular portion of the interior of the substantially round hole, and the flexible sheet is sized to substantially conform with the substantially semi-circular portion of the interior of the substantially round hole.

8. The probe of claim 7, wherein the plurality of sensors extend along a line on the flexible sheet.

9. A probe for an inspection system for a substantially round hole in a material, the probe comprising:

an elongated sensor support;

a bearing plate configured to rotatably support the elongated sensor support in a position in the substantially round hole;

a sensor mount surface shaped to substantially conform with a portion of an interior of the substantially round hole;

a plurality of sensors disposed on the sensor mount surface, each sensor configured to transmit a non-destructive signal into the material for inspecting the substantially round hole; and a biasing element coupling the sensor mount surface and the elongated sensor support, the biasing element biasing the sensor mount surface to substantially conform with the portion of the interior of the substantially round hole.

10. The probe of claim 9, wherein the non-destructive signal includes one of an eddy current signal and an ultrasound signal.

11. The probe of claim 9, wherein the sensor mount surface includes a flexible sheet shaped and biased to substantially conform with a portion of an interior of the substantially round hole.

12. The probe of claim 11, wherein the flexible sheet includes a polystyrene substrate.

13. The probe of claim 9, wherein the sensor mount surface includes a channel along a longitudinal axis thereof, and wherein the plurality of sensors are disposed within the channel.

14. The probe of claim 9, wherein the plurality of sensors extend along a longitudinal line on the sensor mount surface.

15. The probe of claim 9, wherein the bearing plate includes a mount surface configured to mate with an end of the substantially round hole to position the elongated sensor support.

16. The probe of claim 9, wherein the elongated sensor support is rotatably coupled to the bearing plate by a bearing that limits rotation of the elongated bearing support to just greater than 360°.

17. The probe of claim 9, wherein the bearing plate includes at least one passage therethrough.

18. The probe of claim 9, wherein the biasing element includes a plurality of pneumatic rams.

19. The probe of claim 9, wherein the portion includes a substantially semi-circular portion of the interior of the substantially round hole, and the sensor mount surface is sized to substantially conform with the substantially semi-circular portion of the interior of the substantially round hole.

* * * * *